United States Patent [19]

Gallo et al.

[11] Patent Number: 4,647,773

[45] Date of Patent: * Mar. 3, 1987

[54] METHOD OF CONTINUOUS PRODUCTION OF RETROVIRUSES (HTLV-III) FROM PATIENTS WITH AIDS AND PRE-AIDS

[75] Inventors: Robert C. Gallo; Mikulas Popovic, both of Bethesda, Md.

[73] Assignee: The United States of America as represented by the Department of Health and Human Services, Washington, D.C.

[*] Notice: The portion of the term of this patent subsequent to May 28, 2002 has been disclaimed.

[21] Appl. No.: 602,946

[22] Filed: Apr. 23, 1984

[51] Int. Cl.$^4$ .................. C12N 7/02; C12N 7/00; C12N 5/00; C12R 1/91

[52] U.S. Cl. ............................. 435/239; 435/235; 435/240; 435/948; 424/89

[58] Field of Search ............... 435/235, 239, 240, 948, 435/5, 29; 424/89; 128/1 T

[56] References Cited

U.S. PATENT DOCUMENTS 4,464,465  8/1984  Lostrom et al. .................. 435/948
4,520,113  5/1985  Gallo et al. ...................... 435/7

OTHER PUBLICATIONS

Popovic et al, *Science*, 224(4648):497–500, May 4, 1984.
Gallo et al, "Isolation of Human T-Cell Leukemia Virus in Acquired Immune Deficiency Syndrome (AIDS)", Science, 220, pp. 865–867 (5-1983).
Barre-Sinoussi et al, "Isolation of a T-Lymphotropic Retrovirus from a Patient at Risk for AIDS", Science, 220, pp. 868–871 (5-1983).
Marx, "Strong New Candidate for AIDS Agent", Science, 224, pp. 475–477 (5-1984).

*Primary Examiner*—Charles F. Warren
*Assistant Examiner*—John Edward Tarcza
*Attorney, Agent, or Firm*—John S. Roberts, Jr.

[57] ABSTRACT

A cell system is disclosed for the reproducible detection and isolation of human T-lymphotropic retroviruses (HTLV-family) with cytopathic effects (HTLV-III) from patients with the acquired immune deficiency syndrome (AIDS), pre-AIDS and in healthy carriers. One neoplastic aneuploid T-cell line derived from an adult with lymphoid leukemia, and termed HT, was susceptible to infection with the new variants of HTLV, which are transformed and providing T-cell populations which are highly susceptible and permissive from HTLV-III, and convenience for large scale production, isolation and biological detection of the virus.

15 Claims, No Drawings

METHOD OF CONTINUOUS PRODUCTION OF RETROVIRUSES (HTLV-III) FROM PATIENTS WITH AIDS AND PRE-AIDS

The present invention describes a cell system for the reproducible detection and isolation of human T-lymphotropic retroviruses (HTLV-family) with cytopathic or cell killing effects (HTLV-III) from patients with the acquired immune deficiency syndrome (AIDS), pre-AIDS and in healthy carriers. One neoplastic aneuploid T-cell line derived from an adult with lymphoid leukemia, and termed HT, was susceptible to infection with the new variants of HTLV, providing T-cell populations which are highly susceptible and permissive for HTLV-III, and convenience for large scale production, isolation, and biological detection of the virus.

BACKGROUND OF THE INVENTION

The disclosure of this invention is contained in the following journal articles: Gallo et al., "Detection, Isolation, and Continuous Production of Cytopathic Human T-Lymphotropic Retroviruses (HTLV-III) from Patients with AIDS and pre-AIDS," Science, in press; and Gallo et al., "Human T-Lymphotropic Retrovirus, HTLV-III, Isolated from AIDS Patients and Donors at Risk for AIDS," in press.

Epidemiologic data strongly suggest that acquired immune deficiency syndrome (AIDS) is caused by an infectious agent which is apparently horizontally transmitted by intimate contact or blood products. Though the disease is manifested by opportunistic infections, predominantly *Pneumocystis carinii* pneumonia and Kaposi's sarcoma, the underlying disorder affects the patient's cell-mediated immunity with absolute lymphopenia and reduced helper T-lymphocyte (OKT4+) subpopulation(s). Moreover, before a complete clinical manifestation of the disease occurs, its prodrome, pre-AIDS, is frequently characterized by unexplained chronical lymphadenopathy and/or leukopenia involving a helper T cell subset. This leads to the severe immune deficiency of the patient, suggesting that a specific subset of T-cells is the primary target for an infectious agent. Although patients with AIDS or pre-AIDS are often chronically infected with cytomegalovirus or hepatitis B virus, for various reasons these appear to be opportunistic or coincidental infections apparently not linked to the immunological response deficiency. It is believed that the cause of AIDS may be a virus from the family of human T-cell lymphotropic retroviruses (HTLV) which, prior to the present invention, comprised two major well characterized subgroups of human retroviruses, called human T-cell leukemia/lymphoma viruses, HTLV-I and HTLV-II. The most common isolate, HTLV-I, is mainly obtained from patients with mature T-cell malignancies. Seroepidemiological studies, in vitro biological effects, and nucleic acid hybridization data indicate that HTLV-I is etiologically associated with these malignancies, affecting adults primarily in the south of Japan, the Caribbean and Africa. HTLV of subgroup II (HTLV-II) was first isolated from a patient with a T-cell variant of hairy cell leukemia. To date, this is the only reported isolate of HTLV-II from a patient with a neoplastic disease. Virus isolation and seroepidemiological data show that HTLV of both subgroups can sometimes be found in patients with AIDS.

Evidence suggests that the retrovirus(es) of the HTLV family is an etiological agent of AIDS based on the following: (1) there is precedence for an animal retrovirus cause of immune deficiency (feline leukemia virus in cats); (2) retroviruses of the HTLV family are T-cell tropic; (3) they preferentially infect "helper" T-cells (OKT4+); (4) they have cytopathic effects on various human and mammalian cells as demonstrated by their induction of cell syncytia formation; (5) they can alter some T-cell functions; (6) in some cases infection may result in selective T-cell killing; and (7) they are transmitted by intimate contact or through blood products. The presence of antibodies directed to cell membrane antigens of HTLV infected cells has been shown in sera of more than 40% of patients with AIDS [Essex et al., Science, 220:859 (1983)]. This antigen has since been defined as part of the envelope of HTLV [Schüpbach, et al., Science, in press; and Lee, et al., Proc. Nat. Acad. Sci. U.S.A., in press].

The original detection and isolation of the various HTLV isolates were made possible by two earlier developments: the discovery of T-cell growth factor (TCGF), also called Interleukin 2 (Il-2), which enabled the routine selective growth of different subsets of normal and neoplastic mature T-cells [Ruscetti, et al., J. Immunol., 119:131 (1977); and Poiesz, et al., Proc. Nat. Acad. Sci. U.S.A, 77:6134 (1980)] and the development of sensitive assays for detection of retroviruses based on reverse transcriptase assays. The methods of HTLV isolation and transmission involved a cocultivation procedure using permissive T-cells for the virus. The use of normal human T-cells in cocultivation experiments preferentially yielded HTLV of both subgroups with immortalizing (transforming) capability for some of the target T-cells.

However, HTLV variants (now termed HTLV-III), lack immortalizing properties for normal T-cells and mainly exhibit cytopathic effects on the T-cells and is now believed to be the cause of AIDS. In fact, such variants were frequently but only transiently detected using these normal T-cells as targets in cocultivation or cell-free transmission experiments. The cytopathic effect was overcome by finding a highly susceptible, permissive cell for cytopathic variants of HTLV, thus preserving the capacity for permanent growth after infection with the virus. The present invention discloses the identification and characterization of this new immortalized T-cell population and its use in the isolation and continuous high-level production of such viruses from patients with AIDS and pre-AIDS.

Early experiments identified one neoplastic aneuploid T-cell line, termed HT, derived from an adult with lymphoid leukemia, that was susceptible to infection with the new cytopathic virus isolates.

This cell line is a sensitive target for transmission of these virus isolates (HTLV-III) and it allows continuous large-scale virus production and development of specific immunologic reagents and nucleic acid probes useful for comparison of these new isolates among themselves and with HTLV-I and HTLV-II. In addition to their differences in biological effects that distinguish them from HTLV-I and HTLV-II, HTLV-III also differs from these known HTLV subgroups in several immunological assays and in morphology. However, these new retroviruses are T4 lymphotropic and exhibit many properties similar to HTLV-I and II, including similar properties of the reverse transcriptase, cross reactivity of structural proteins as determined by heterologous competition radioimmune assays with patients' sera and with animal hyperimmune sera, and induction of syncytia. These new retrovirus isolates are collectively designated HTLV-III, together with detectable differences in some of their proteins and genetic information, HTLV-III's ability to kill T-cells clearly separates these variants from other members of the HTLV family.

STATEMENT OF DEPOSIT

A cell line corresponding to the present invention, and denoted H9/HTLV-III$_B$, has been deposited in the ATCC (under ATCC No. CRL 8543) on Apr. 19, 1984, prior to the filing of this patent application. This deposit assures permanence of the deposit and ready accessibility thereto by the public. H9 is a representative and preferred cell line in accordance with the invention.

UTILITY STATEMENT

The cell line which is a product of the present invention (H9/HTLV-III$_B$) is presently useful for the production of vaccines for the relief of AIDS and for the detection of antibodies to the virus in blood samples.

GENERAL DESCRIPTION

A susceptible cell line HT was tested for HTLV before in vitro infection and it was negative by all criteria, including lack of proviral sequences. Continuous production of HTLV-III is obtained after repeated exposure of parental HT cells ($3 \times 10^6$ cells pretreated with polybrene) to concentrated culture fluids containing HTLV-III harvested from short term cultured T-cells (grown with TCGF) which originated from patients with pre-AIDS or AIDS. The concentrated fluids were first shown to contain particle associated reverse transcriptase (RT). When cell proliferation declined, usually 10 to 20 days after exposure to the culture fluids, the fresh (uninfected) HT parental cells are added to cultures. Culture fluids from the infected parental cell line was positive for particulate RT activity and about 20% of the infected cell population was positive in an indirect immune fluorescent assay (IFA) using serum from a hemophilia patient with pre-AIDS (patient E.T.). Serum from E.T. also contained antibodies to proteins of disrupted HTLV-III but did not react with proteins of HTLV-I or HTLV-II infected cells.

SPECIFIC DISCLOSURE

As has been mentioned above, an aneuploid HT-cell line exhibited the desired prerequisites for the continuous propagation of HTLV-III. This cell line is a neoplastic aneuploid T-cell line derived from an adult patient with lymphoid leukemia, selected for its mature T-cell phenotype [OKT3+ (62%), OKT4+ (39%) and OKT8−], as determined by cytofluorometry using a fluorescence-activated cell sorter. Cultures of these cells are routinely maintained in RPMI/1640 with 20% fetal calf serum and antibiotics. These cultures are shown in Example 1, Table 1. Clone H9 is preferred, with Clone H4 being secondarily preferred.

HTLV-III culture fluids are isolated from cultured cells of patients with acquired immune deficiency syndrome (AIDS). Peripheral blood leukocytes from these patients are banded in Ficoll-Hypaque, incubated in growth media (RPMI 1640, 20% fetal bovine serum 0.29 mg/ml glutamine) containing 5 μg/ml phytohemagglutinin (PHA-P) for 48 hours, at 37° C. in a 5% $CO_2$ atmosphere. The leukocytes are then refed with growth medium containing 10% purified T cell growth factor (TCGF); optionally, some of the cells also received rabbit antibody to alpha interferon. Cells and growth media from these lymphocytes are then assayed for the presence of HTLV subgroups I-III. Samples exhibiting more than one of the following were considered positive: repeated detection of a $Mg^{++}$ dependent reverse transcriptase activity in supernatant fluids; virus observed by electron microscopy; intracellular expression of virus-related antigens detected with antibodies from sero-positive donors or with hyperimmune serum; or transmission of particles, detected by reverse transcriptase assays or by electron microscopic observation, to fresh human cord blood, bone marrow, or peripheral blood T-lymphocytes. All isolates not classified as either HTLV-I or HTLV-II by immunological or nucleic acid analysis were classified as HTLV-III. The cells in the HTLV-III producing cell cultures, characterized using established immunological procedures, are predominantly T-lymphocytes (E rosette receptor, OKT/3 and Leu/1 positive, with a T4 phenotype (OKT4, leu 3a positive). This process is also described by Gallo, et al., in *Science*, 220:865–867 (1983).

The infection of parental HT cells as well as other cloned cell populations occurs by exposure of these cells to concentrated or nonconcentrated culture fluids (cell-free infection) from T-cell cultures from AIDS or pre-AIDS patients, or by cocultivation; that is, HT cells are infected by exposure to HTLV-III containing cultures. The usual cell-free infection procedure is as follows: 2 to $5 \times 10^6$ cells are treated with polybrene (2 μg/ml) or DEAE dextran for 30 minutes in $CO_2$ incubator at 37° C., and then exposed to the virus inoculum (0.1 to 1 ml) for one hour in the incubator ($CO_2/37°$ C.). The cells are kept in suspension by shaking at regular intervals. After one hour of incubation a regular growth medium is added. The positivity of infected cultures for HTLV-III is assessed after one, two, and three weeks of cultivation.

The infection of HT cells (clones) is also obtained by cocultivation procedure—HT cells are mixed in various proportions (usually 1:5) with short- term cultured T-cells (about 5 to 20 days) from AIDS or pre-AIDS patients. The positivity for HTLV-III was scored by the detection of viral antigens or viral nucleic acid sequences in the infected recipient cells at various intervals (7, 14, 21 days, etc.) after cocultivation. The mixed cultures are maintained in growth medium for several months.

EXAMPLE 1

As shown in Table 1 below, single cell HT clones were isolated as described by Popovic, et al., in *Neoplasma*, 18:257 (1971), and Bach, et al., *Immunol. Rev.*, 54:5 (1981) from a long-term cultured aneuploid HT-cell line exhibiting mature T-cell phenotype (OKT3+ [62%], OKT4+ [39%] and OKT8−) as determined by cytofluorometry using a fluorescence-activated cell sorter. The cultures were routinely maintained in RPMI/1640 with 20% fetal calf serum and antibiotics. The terminal cell density of the parental cell culture, seeded at a concentration of $2 \times 10^5$ cells/milliliter of culture media, was in the range $10^6$–$1.5 \times 10^6$ cells/ml after 5 days of culture.

For detection of multinucleated cells, cell smears were prepared from cultures 6 and 14 days after infection and stained with Wright-Giemsa. Cells having more than 5 nuclei were considered as multi-nucleated cells. Cloned cells from uninfected cultures also contained some multi-nucleated giant cells as well; however, the arrangement of multiple nuclei in a characteristic ring formation was lacking and the number of these Triton X-100/1.5M KCl. Reverse transcriptase (RT) assays were performed as described by Poiesz, et al., Proc Nat. Acad. Sci. U.S.A., 77:7415 (1980) and expressed in cpm per milliliter culture medium.

TABLE 1

| Characteristics | Response of Cloned T-Cell Populations to HTLV-III Infection | | | | | | | |
|---|---|---|---|---|---|---|---|---|
| | Clones | | | | | | | |
| | H3 | H4 | H6 | H9 | H17 | H31 | H35 | H38 |
| Total cell number ($\times 10^6$) | | | | | | | | |
| 6 days after infection | 1 | 1.5 | 1.5 | 0.3 | 0.4 | 0.3 | 0.5 | 1.8 |
| 14 days after infection | 2.2 | 7.3 | 7.5 | 10.0 | 4.7 | 5.0 | 4.5 | 3.2 |
| Multinucleated cells (%) | | | | | | | | |
| 6 days after infection | 24 | 42 | 32 | 7 | 13 | 14 | 30 | 45 |
| 14 days after infection | 45 | 48 | 45 | 30 | 22 | 45 | 60 | 60 |
| Immunofluorescence positive cells (%) | | | | | | | | |
| 6 days after infection | | | | | | | | |
| Rabbit antiserum to HTLV-III | 55 | 56 | 32 | 32 | 39 | 21 | 10 | 87 |
| Patient serum (E.T.) | 56 | 29 | 21 | ND | ND | ND | ND | 73 |
| 14 days after infection | | | | | | | | |
| Rabbit antiserum to HTLV-III | 50 | 74 | 60 | 97 | 71 | 40 | 20 | 80 |
| Patient serum | 45 | 47 | 56 | 78 | 61 | 43 | 22 | 89 |
| Reverse transcriptase activity ($\times 10^4$ cpm/ml) | | | | | | | | |
| 6 days after infection | 2.4 | 1.8 | 2.1 | 4.1 | 2.6 | 1.4 | 1.7 | 2.5 |
| 14 days after infection | 16.2 | 18.1 | 16.1 | 20.2 | 17.1 | 13.4 | 15.1 | 18.2 |

ND = not done cells was much less (0.7% to 10%).

Immunofluorescence positive cells were washed with phosphate-buffered saline (PBS) and resuspended in the same buffer at concentration $10^6$ cells per milliliter. Approximately 50 λ of cell suspension were spotted on slides, air dried, and fixed in acetone for 10 min. at room temperature. Slides were stored at −20° C. until use. Twenty microliters of either hyperimmune rabbit antiserum to HTLV-III (diluted 1/2000 in PBS) or serum from the patient (E.T.) diluted 1/8 in PBS was applied to cells and incubated for 50 min. at 37° C. The fluorescein-conjugated antiserum to rabbit or human immunogloblin G was diluted and applied to the fixed cells for 30 min. at room temperature. Slides then were washed extensively before microscopic examinations. The uninfected parental cell line as well as the clones were consistently negative in these assays.

To determine reverse transcriptase activity, virus particles were precipitated from cell-free supernatant as follows: 0.4 ml of 4M NaCl and 3.6 ml of 30% (wt/vol.) polyethylene glycol (Carbowax 6000) were added to 8 ml of harvested culture fluids and the suspension was placed on ice overnight. The suspension was centrifuged in a Sorvall RC-3 centrifuge at 2000 rpm at 4° C. for 30 min. The precipitate was resuspended in 300 μl at 50% (vol/vol) glycerol (25 mM Tris-HCl, pH 7.5/5mM dithiothreitol/150 mM KCl/0.025% Triton X-100. Particles were disrupted by addition of 100 μl of 0.9%

EXAMPLE 2

As shown in Table 2 below, cocultivation with H4 recipient T-cell clone was performed with fresh mononuclear cells from peripheral blood of patients RF and SN, respectively. In the case of patients BK and LS cocultivation was performed with T-cells grown in the presence of exogenous TCGF (10% V/V) for 10 days. The ratio recipient/donor (patients') cells was 1:5. The mixed cultures were maintained in RPMI/1640 (20% FCS and antibiotics) in the absence of exogenous TCGF. Cell free infection of H9 T-cell clone was performed using concentrated culture fluids harvested from T-cell cultures of the patient WT. The T-cell cultures were grown in the presence of exogenous TCGF for two weeks before the culture fluids were harvested and concentrated. Cells of H9 clones were pretreated with polybrene (2 μg/ml) for 20 min. and $2 \times 10^6$ cells were exposed for one hr. to 0.5 ml of 100-fold concentrated culture fluids positive for particulate RT activity.

HTLV-III virus expression in both cocultured and cell-free infected cell cultures were assayed approximately one month after in vitro cultivation. There was considerable fluctuation in HTLV-III expression (see Table 2). For details of both reverse transcriptase (RT) assays and indirect immunofluorescence assays (IFA) see Example 1.

TABLE 2

| | Isolation of HTLV-III from Patients with Pre-AIDS and AIDS | | | | | |
|---|---|---|---|---|---|---|
| | | | Virus Expression | | | |
| | | | | IFA with | | |
| Patient | Diagnosis | Origin | RT Activity ($\times$ 10 cpm) | Rabbit Serum (% Positive) | Human Serum (ET) (% Positive) | EM |
| RF | AIDS (heterosexual) | Haiti | 0.25 | 80 | 33 | ND |
| SN | Hemophiliac (lymphadenopathy) | U.S. | 6.3 | 10 | ND | + |
| BK | AIDS (homosexual) | U.S. | 0.24 | 44 | 5 | + |
| LS | AIDS (homosexual) | U.S. | 0.13 | 64 | 19 | + |

TABLE 2-continued

Isolation of HTLV-III from Patients with Pre-AIDS and AIDS

| | | | | Virus Expression | | |
| | | | | | IFA with | |
| Patient | Diagnosis | Origin | RT Activity ($\times$ 10 cpm) | Rabbit Serum (% Positive) | Human Serum (ET) (% Positive) | EM |
| --- | --- | --- | --- | --- | --- | --- |
| WT | Hemophiliac (lymphadenopathy) | U.S. | 3.2 | 69 | ND | ND |

RT = reverse transcriptase
IFA = immunofluorescence assays
EM = electron microscopy
ND = not done

EXAMPLE 3

To select for high permissiveness for HTLV-III and to preserve permanent growth and continuous production of virus, extensive cloning of the HT parental T-cell population was performed. A total of 51 single-cell clones was obtained by both capillary and limited dilution techniques using irradiated mononuclear cells from peripheral blood of a healthy donor as a feeder. The growth of these cell clones was compared after HTLV-III infection. A representative example of response to virus infection of 8 T-cell clones which are susceptible to and permissive for HTLV-III is shown in Table 1. In parallel experiments, $2 \times 10^6$ cells of each T-cell clone were exposed to 0.1 ml of concentrated virus. Then cell growth and morphology, expression of cellular viral antigen(s), and RT activity in culture fluids were assessed 6 and 14 days after infection. Although all 8 clones were susceptible to and permissive for the virus, there were considerable differences in their ability to proliferate after infection. The cell number decreased by 10% to 90% from the initial cell count within 6 days after infection, and a high proportion of multinucleated (giant) cells were consistently found in all 8 infected clones. The percentage of T-cells positive for viral antigen(s) determined by immunofluorescent assays with serum from AIDS patient (E.T.) and with hyperimmune rabbit serum raised against the whole disrupted HTLV-III ranged from 10% to over 80%. Fourteen days after infection, the total cell number and the proportion of HTLV-III positive cells increased in all 8 clones. The virus positive cultures consistently showed round giant cells which contained numerous nuclei. These multinucleataed giant cells are similar to those induced by HTLV-I and HTLV-II except that the nuclei exhibit a characteristic ring formation. Electron microscopic examinations showed that the cells released considerable amounts of virus.

EXAMPLE 4

To determine whether HTLV-III is continuously produced by the infected T-cells in long-term cultures, both virus production and cell viability of the infected clone, H4, were followed for several months. Although the virus production fluctuated, culture fluids harvested from the H4/HTLV-III cell cultures at approximately 14-day intervals consistently exhibited particulate RT activity which has been followed for over 5 months. The viability of the cells ranged from 65% to 85% and a doubling time of the cell population, which is called H4/HTLV-III, was approximately 30-40 hours. Thus, this permanently growing T-cell population can continuously produce HTLV-III.

The yield of virus produced by H4/HTLV-III cells was assessed by purification of concentrated culture fluids through a sucrose density gradient and assays of particulate RT activity in each fraction collected from the gradient. The highest RT activity was found at density 1.16 g/ml, similar to other retroviruses.

We claim:

1. A method for continuous production of HTLV-III virus which comprises infecting in cell culture highly susceptible, permissive cells consisting of a neoplastic aneuploid HT-cell line with said virus, said cells preserve the capacity for permanent growth after the infection with said virus, growing said cells under conditions suitable for cell growth and recovering said virus produced by said cells.

2. The method of claim 1, wherein said virus consists of cytopathic variants of HTLV.

3. The method of claim 1 wherein said infecting comprises cocultivating said virus with said cells to produce a cell line and recovering said cell line.

4. The method of claim 1 wherein said infecting comprises cell-free infection of said cells with said virus.

5. The method of claim 1 wherein said cells are neoplastic aneuploid T-cells derived from an adult with lymphoid leukemia.

6. A process for the continuous production of HTLV-III virus which comprises cocultivating said virus with a target HT-cell to produce an infected cell line, growing said cell line and recovering said virus from supernatants produced by said cell line.

7. The process of claim 6 wherein said target T-cell is a neoplastic aneuploid T-cell susceptible to infection with HTLV-III.

8. A process for the continual production of HTLV-III by infecting T-cells in cultures which comprises cocultivating HTLV-III virus with an HT-clone to produce an infected cell line, said clone being an aneuploid T-cell line derived from lymphoid leukemia, growing said cell line and recovering said virus from supernatants produced by said cell line.

9. The process in claim 8 wherein said clone is a mature T-cell phenotype of OKT3+ (62%), OKT4+ (39%) and OKT8−.

10. A method of producing a cell line containing an antigen of HTLV-III which compries infecting an HT-cell line derived from lymphoid leukemia and susceptible to infection with HTLV-III, said cell line is capable of continuous large-scale production of HTLV-III, and growing the infected cell line under conditions suitable for growth.

11. The method of claim 10 wherein said cell line is a neoplastic aneuploid T-cell line.

12. The method of claim 10 wherein said HTLV-III are variants of human T-lymphotropic retrovirus, exhibit cytopathic effects and are non-transforming.

13. A cell line containing HTLV-III designated H9/HTLV-III$_B$, ATCC Accession CRL 8543.

14. A process for producing a cell line H9/HTLV-III$_B$ which comprises infecting a target T-cell with HTLV-III virus to produce a cell line and recovering same, said infecting process overcomes the normal cytopathic effect of HTLV-III and preserves the immortal growth capacity of the target cell.

15. An HT cell line permanently infected with HTLV-III virus, wherein said cell line continually produces said virus.

* * * * *